United States Patent
Gebhardt et al.

(10) Patent No.: US 11,168,060 B2
(45) Date of Patent: Nov. 9, 2021

(54) METHOD FOR PRODUCING 2-[4-(4-CHLOROPHENOXY)-2-(TRIFLUOROMETHYL)PHENYL]-1-(1,2,4-TRIAZOL-1-YL)PROPAN-2-OL

(71) Applicant: BASF Agro B.V., Arnhem (NL)

(72) Inventors: Joachim Gebhardt, Ludwigshafen (DE); Daniel Saelinger, Ludwigshafen (DE); Manfred Ehresmann, Maxdorf (DE); Roland Goetz, Neulussheim (DE)

(73) Assignee: BASF AGRO B.V., Arnhem (NL)

( * ) Notice: Subject to any disclaimer, the term of this patent is extended or adjusted under 35 U.S.C. 154(b) by 661 days.

(21) Appl. No.: 16/062,828

(22) PCT Filed: Dec. 15, 2016

(86) PCT No.: PCT/EP2016/081113
§ 371 (c)(1),
(2) Date: Jun. 15, 2018

(87) PCT Pub. No.: WO2017/102905
PCT Pub. Date: Jun. 22, 2017

(65) Prior Publication Data
US 2021/0214319 A1    Jul. 15, 2021

(30) Foreign Application Priority Data
Dec. 18, 2015 (EP) ..................................... 15201269

(51) Int. Cl.
*C07D 249/08* (2006.01)

(52) U.S. Cl.
CPC ........ *C07D 249/08* (2013.01); *C07B 2200/13* (2013.01)

(58) Field of Classification Search
CPC .................................................... C07D 249/08
See application file for complete search history.

(56) References Cited

FOREIGN PATENT DOCUMENTS

| WO | 09069140 A1 | 6/2009 |
|---|---|---|
| WO | 13007767 A1 | 1/2013 |
| WO | 14108286 A1 | 7/2014 |
| WO | 15091045 A1 | 6/2015 |
| WO | 16005211 A1 | 1/2016 |
| WO | 16202807 A1 | 12/2016 |

OTHER PUBLICATIONS

Search Report, issued in EP Application No. 15201269.6, dated Aug. 1, 2016.
International Search Report, issued in PCT/EP2016/081113, dated Feb. 24, 2017.
International Preliminary Report on Patentability, issued in PCT/EP2016/081113, dated Nov. 24, 2017.

*Primary Examiner* — Patricia L Morris

(57) ABSTRACT

The present invention relates to a method for producing 2-[4-(4-chlorophenoxy)-2-(trifluoromethyl)phenyl]-1-(1,2,4-triazol-1-yl)propan-2-ol in high purity. Especially it relates to a method in which this compound is effectively separated from its 1,2,4-triazol-4-yl isomer.

22 Claims, No Drawings

METHOD FOR PRODUCING 2-[4-(4-CHLOROPHENOXY)-2-(TRIFLUOROMETHYL)PHENYL]-1-(1,2,4-TRIAZOL-1-YL)PROPAN-2-OL

This application is a National Stage application of International Application No. PCT/EP2016/081113, filed Dec. 15, 2016. This application also claims priority under 35 U.S.C. § 119 to European Patent Application No. 15201269.6, filed Dec. 18, 2015.

The present invention relates to a method for producing 2-[4-(4-chlorophenoxy)-2-(trifluoromethyl)phenyl]-1-(1,2,4-triazol-1-yl)propan-2-ol in high purity. Especially it relates to a method in which this compound is effectively separated from its 1,2,4-triazol-4-yl isomer.

2-[4-(4-Chlorophenoxy)-2-(trifluoromethyl)phenyl]-1-(1,2,4-triazol-1-yl)propan-2-ol is an effective fungicide described, for example, in WO 2014/108286 and WO 2015/091045. It is generally synthesized from 2-[4-(4-chlorophenoxy)-2-(trifluoromethyl)phenyl]-2-methyl-oxirane which is reacted with 1H-[1,2,4]-triazole. The reaction is however not perfectly selective; apart from the desired 1,2,4-triazol-1-yl compound, the 1,2,4-triazol-4-yl isomer (i.e. the corresponding compound, in which the triazole ring is however bound via its 4-position to the remainder of the molecule) is formed, too. WO 2013/007767 describes the synthesis of 2-[4-(4-Chlorophenoxy)-2-(trifluoromethyl)phenyl]-1-(1,2,4-triazol-1-yl)propan-2-ol.

WO 2009/0691340 relates to a process for the preparation of the non-steroidal aromatase inhibitor drug Letrozole and its intermediates. In agricultural chemistry, it is generally regarded as essential to provide active ingredients in high purity in order to ensure a high reliability of the product and avoid unexpected and undesired side effects stemming from side products or other impurities.

WO 2014/108286 describes a method for synthesizing 2-[4-(4-chlorophenoxy)-2-(trifluoromethyl)phenyl]-1-(1,2,4-triazol-1-yl)propan-2-ol by reaction of the respective oxirane with 1H-[1,2,4]-triazole. The reaction is generally carried out in dimethylformamide, dimethylacetamide or N-methylpyrrolidone. After completion of the reaction the solvent is evaporated in large part; e.g. at least 55% or, as realized in the experimental part, about 80% of the solvent are removed. Then water and an unpolar solvent, specifically toluene, are added, and the desired product is crystallized directly from the concentrated toluene mixture. From the experimental part it is however not discernible how well this process works, as the reported results are ambiguous.

One problem arising with this method is that that portion of the polar solvent used in the reaction of the oxirane with the triazole which has not been evaporated moves at least partly to the water phase in the extraction step and is removed with this. On the one hand such water/polar aprotic solvent mixtures cannot be disposed as such as they are environmentally problematic. Moreover, it is desired to recover as much solvent as possible in order to be able to recycle this and waste less. On the other hand, the separation of water/polar aprotic solvent mixtures is cumbersome and energy-consuming, as the polar aprotic solvents used in this reference all have a boiling point above that of water.

As the inventors of the present application found out, removing the polar aprotic solvent completely after the completion of the reaction is not a solution, as the purity of the desired product decreases unsatisfactorily.

It was therefore the object of the present invention to provide a method which yields 2-[4-(4-chlorophenoxy)-2-(trifluoromethyl)phenyl]-1-(1,2,4-triazol-1-yl)propan-2-ol in high purity and especially with a negligible amount of the undesired 1,2,4-triazol-4-yl isomer (i.e. of 2-[4-(4-chlorophenoxy)-2-(trifluoromethyl)phenyl]-1-(1,2,4-triazol-4-yl)propan-2-ol); and which moreover avoids the production of waste water containing significant amounts of the polar aprotic solvent used in the reaction of 2-[4-(4-chlorophenoxy)-2-(trifluoromethyl)phenyl]-2-methyl-oxirane with 1H-[1,2,4]-triazole.

In a first aspect the present invention relates to a method (method A) for obtaining 2-[4-(4-chlorophenoxy)-2-(trifluoromethyl)phenyl]-1-(1,2,4-triazol-1-yl)propan-2-ol of formula (I) from a mixture containing the compound of formula (I) and 2-[4-(4-chlorophenoxy)-2-(trifluoromethyl)phenyl]-1-(1,2,4-triazol-4-yl)propan-2-ol of formula (I-sym)

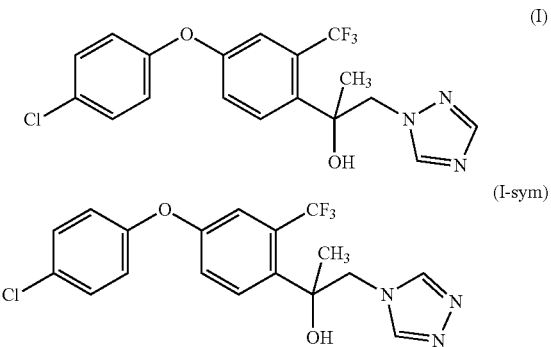

which method comprises
(a) providing a mixture containing the compounds of formulae (I) and (I-sym) in at least one aromatic solvent, where the mixture contains the compound of formula (I) in a concentration of from 30 to 90% by weight, relative to the total weight of the mixture;
(b) adding to the mixture of step (a) at least one polar aprotic solvent, so that it is contained in an amount of from 1 to 25% by weight, relative to the weight of the solution obtained after the addition of the at least one polar aprotic solvent; and
(c) crystallizing the compound of formula (I) from the mixture obtained in step (b).

The mixture provided in step (a) may comprise, apart from compounds (I) and (I-sym) and the at least one aromatic solvent, impurities, such as unreacted starting material from which compounds (I) and (I-sym) are formed. They may also comprise traces of other organic solvents (i.e. solvents different from the aromatic solvent(s) used in step (a)). These impurities and other organic solvents, if present, are however contained in minor amounts, preferably in an overall amount of at most 15% by weight, more preferably at most 10% by weight, in particular at most 5% by weight, relative to the overall weight of the mixture. Especially the other organic solvents, if present, are contained in an amount of at most 10% by weight, preferably at most 8% by weight, in particular at most 5% by weight, specifically at most 2% by weight, relative to the overall weight of the mixture.

Mixtures containing compounds (I) and (I-sym) are generally formed when the compound (I) is prepared by nucleophilic addition of or substitution by 1H-[1,2,4]-triazole to/at an electrophilic carbon atom of a precursor molecule of compound (I). For instance, such mixtures are generally formed when 2-[4-(4-chlorophenoxy)-2-(trifluoromethyl)phenyl]-2-methyl-oxirane is reacted with 1H-[1,2,4]-triazole.

Thus, in a second aspect, the present invention relates to a method (method B) for the preparation of 2-[4-(4-chlorophenoxy)-2-(trifluoromethyl)phenyl]-1-(1,2,4-triazol-1-yl)propan-2-ol of formula (I)

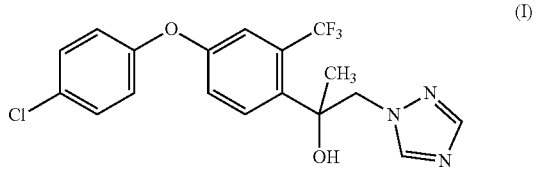 [SMILES: CC(O)(Cn1cncn1)c1ccc(Oc2ccc(Cl)cc2)cc1C(F)(F)F]
(I)

comprising following steps:
(i) reacting 2-[4-(4-chlorophenoxy)-2-(trifluoromethyl)phenyl]-2-methyl-oxirane of formula (II)

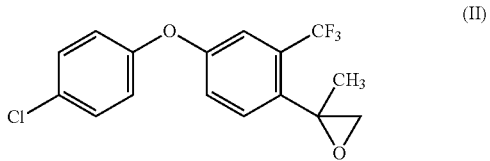 [SMILES: CC1(c2ccc(Oc3ccc(Cl)cc3)cc2C(F)(F)F)CO1]
(II)

with 1H-[1,2,4]-triazole in the presence of a base in at least one polar aprotic solvent;
(ii) after completion of the reaction removing at least 90% of the polar aprotic solvent;
(iii) diluting the mixture obtained in step (ii) with at least one aromatic solvent and extracting the diluted mixture with water or an aqueous solution;
(iv) if necessary removing a part of the aromatic solvent introduced in step (iii) from the organic phase obtained in step (iii) to such an extent that the resulting mixture contains the compound (I) in a concentration of from 30 to 90% by weight, relative to the total weight of the mixture;
(v) adding to the mixture obtained in step (iii) or (iv) at least one polar aprotic solvent so that it is contained in an amount of from 1 to 25% by weight, relative to the weight of the mixture obtained after the addition of the at least one polar aprotic solvent; and
(vi) crystallizing the compound of formula (I) from the mixture obtained in step (v).

In step (i) of method B 1H-[1,2,4]-triazole is preferably used in at least equimolar amounts with respect to the oxirane (II). Preferably, the oxirane (II) and 1H-[1,2,4]-triazole are used in a molar ratio of from 1:1 to 1:4, more preferably from 1:1 to 1:3, in particular from 1:1.1 to 1:2, more particularly from 1:1.1 to 1:1.5 and specifically from 1:1.1 to 1:1.35.

The base used in step (i) can be an inorganic or organic base. Inorganic bases are for example alkali and earth alkaline hydroxides, carbonates, hydrogen carbonates, phosphates and hydrogen phosphates. Organic bases are for example pyridine, substituted pyridines, like lutidine or 4-(dimethylamino)-pyridine, tertiary amines, like triethylamine, tripropylamine, diisopropylethylamine or morpholine, or cyclic amidines, like 1,4-diazabicyclo[2.2.2]octan (DABCO), 1,8-diazabicyclo[5.4.0]undec-7-ene (DBU) or 1,5-diazabicyclo(4.3.0)non-5-ene (DBN).

Preferably, however, inorganic bases are used. Preferred inorganic bases are alkali metal hydroxides, carbonates and phosphates, especially LiOH, NaOH, KOH, $Li_2CO_3$, $Na_2CO_3$, $K_2CO_3$, $Cs_2CO_3$, $Li_3PO_4$, $Na_3PO_4$ or $K_3PO_4$. In particular alkali metal hydroxides, and especially NaOH or KOH are used. Very specifically NaOH is used.

In a specific embodiment at least a part of 1H-[1,2,4]-triazole is used as the corresponding alkali metal salt, e.g. as its $Li^+$, $Na^+$ or $K^+$ salt. This is obtained by reacting 1H-[1,2,4]-triazole with the respective hydroxide (i.e. LiOH, NaOH or KOH), hydride (LiH or NaH) or alcoholate (e.g. sodium or potassium methanolate, ethanolate or tert-butanolate) and isolating it before introducing it into the reaction of step (i).

Strong bases, i.e. bases with a $pK_b$ below 3.75, are preferably used in at most stoichiometric amounts with respect to the oxirane (II). In case of bases derived from polybasic acids, such as the carbonates and phosphates, and also in case of bases derived from monobasic acids, but with a two or three times charged counter cation, such as earth alkaline hydroxides, e.g. $Ca(OH)_2$, the term "stoichiometric" takes of course into consideration how many protons the base can neutralize. For instance, in case of an alkali metal hydroxide, stoichiometric amounts with respect to oxirane (II) means a molar ratio of 1:1, while in case of alkali or earth alkaline metal carbonates or of earth alkaline metal hydroxides stoichiometric amounts with respect to oxirane (II) mean a molar ratio of oxirane to base of 2:1, and in case of alkali metal phosphates stoichiometric amounts with respect to oxirane (II) mean a molar ratio of oxirane to phosphate of 3:1.

Weaker bases (i.e. bases with a $pK_b$ of at least 3.75) are preferably used in at least stoichiometric amounts. For "stoichiometric amounts" in case of bases derived from polybasic acids the above remarks apply.

In case of bases derived from strong monobasic acids and with a monovalent counter cation, here the alkali metal hydroxides, the base is preferably used in an amount of from 0.2 to 1 mol per mol of oxirane (II), in particular from 0.3 to 0.7 mol per mol of oxirane (II).

Step (i) is generally carried out at from 100° C. to the boiling point of the reaction mixture. It has however been found that the compound of formula (I) is obtained in higher purity if the reaction in step (i) is carried out at from 110 to 130° C., in particular from 110 to 120° C. and specifically from 110 to 115° C.

Aprotic solvents are solvents without a functional group from which a proton can dissociate. Polar solvents are solvents with a dielectric constant of greater than 15. Polar aprotic solvents combine both properties. Examples for polar aprotic solvents are amides, such as N,N-dimethylformamide (DMF) and N,N-dimethylacetamide; sulfoxides, such as dimethylsulfoxide (DMSO); lactams, such as N-methylpyrrolidone (NMP); cyclic ethers, such as tetrahydrofuran, 1,3-dioxane and 1,4-dioxane; ketones such as acetone and methylethylketone; nitriles, such as acetonitrile; lactones, such as γ-butyrolactone; nitro compounds, such as nitromethane; ureas, such as tetramethyl urea or dimethylpropylene urea (DMPU), sulfones, such as sulfolan, and carbonic acids, such as dimethylcarbonate or ethylenecarbonate.

The at least one polar aprotic solvent used in step (i) and (v) can be the same or different. Preferably, the at least one polar aprotic solvent used in step (b), (i) and (v) is independently selected from N,N-dimethylformamide, N,N-dimethylacetamide, dimethylsulfoxide, N-methylpyrrolidone, tetrahydrofuran, 1,4-dioxane, acetone, methylethylketone, acetonitrile and mixtures thereof. More preferably, the at least one polar aprotic solvent used in step (b), (i) and (v) is independently selected from N,N-dimethylformamide, N,N- dimethylacetamide, dimethylsulfoxide and N-methylpyrrolidone. In particular, the at least one polar aprotic solvent used in step (i) is selected from N,N-dimethylformamide, N,N-dimethylacetamide, dimethylsulfoxide and N-methylpyrrolidone, and the at least one polar aprotic solvent used in step (b) and (v) is N,N-dimethylformamide. Specifically, the polar aprotic solvent used in step (b), (i) and (v) is N,N-dimethylformamide.

According to another embodiment, the at least one polar aprotic solvent used in step (i) is selected from N,N-dimethylformamide, N,N-dimethylacetamide, dimethylsulfoxide and N-methylpyrrolidone, and the at least one polar aprotic solvent used in step (b) and (v) is N,N-dimethylformamide or N-methylpyrrolidone. Specifically, according to this embodiment, the polar aprotic solvent used in step (b), (i) and (v) is N,N-dimethylformamide or N-methylpyrrolidone. In step (ii), after completion of the reaction, all or at least almost all of the polar aprotic solvent(s), i.e. at least 90%, preferably at least 92%, in particular at least 95% and specifically at least 98% of the polar aprotic solvent(s) are removed. The percentages relate to the amount of solvent(s) introduced in step (i) (which is considered as 100%). If step (i) has been carried out under high dilution, the minimum amount of solvent to be removed, so that the condition of step (v) can be met and the object of the invention to avoid the production of water/polar aprotic solvent(s) mixtures can be achieved, is of course necessarily closer to 100% than in cases where step (i) has been carried out in high concentration. Preferably the polar aprotic solvent(s) is/are removed to such an extent that in the resulting mixture the weight ratio of remaining polar aprotic solvent(s) to theoretically present compound (I) (i.e. if the yield is 100%) is at most 1:3, i.e. from 1:3 to 0:1, more preferably at most 1:4, i.e. from 1:4 to 0:1, in particular at most 1:7, i.e. from 1:7 to 0:1, more particularly at most 1:9, i.e. from 1:9 to 0:1, even more particularly at most 1:19, i.e. from 1:19 to 0:1, and specifically at most 1:24, i.e. from 1:24 to 0:1. The solvent(s) is/are generally removed by distillation.

The temperature used for distillation does preferably not exceed the reaction temperature of step (i). Thus, distillation is preferably carried out under reduced pressure. The amount of removed solvent(s) can be determined, for example, by weighing the amount of removed solvent(s) and comparing it to the amount introduced in step (i), or by gas chromatography of the reaction mixture obtained after removal of the solvent(s).

"Completion of the reaction" means that the reaction is carried out until no oxirane (II) can be detected anymore. Detection can be accomplished by standard methods, such as TLC, GC, HPLC or NMR of a sample of the reaction mixture.

The polar aprotic solvent(s) removed in step (ii) can be recycled and used again in step (i), if necessary after a purification step, e.g. via rectification.

In step (iii) the mixture obtained in step (ii) is diluted with at least one aromatic solvent and the diluted mixture is extracted with an aqueous medium, i.e. with water or an aqueous solution. Aqueous extraction is carried out in order to remove any salts formed, if present, excess base, if present, excess 1H-[1,2,4]-triazole, if present, remainders of the polar aprotic solvent(s), if present, and any other water-soluble components, if present. The at least one aromatic solvent can be added first and water or an aqueous solution can be added subsequently to the mixture obtained in step (ii), or inversely, or the at least one aromatic solvent and water or the aqueous solution can be added simultaneously.

The at least one aromatic solvent used in step (iii) is preferably selected from benzene, toluene, the xylenes and mixtures thereof; and is in particular toluene.

The aqueous solution is for example brine (saturated aqueous sodium chloride solution), non-saturated aqueous sodium chloride solution, or an acidic solution, e.g. diluted aqueous HCl.

Preferably the extracting agent is water or brine and is in particular water.

In a preferred embodiment, the extraction in step (iii) is carried out at from 50 to 90° C., in particular from 70 to 90° C. For this purpose, preferably, the at least one aromatic solvent is added to the mixture obtained in step (ii), the mixture is heated to a temperature of from 50 to 90° C., in particular from 70 to 90° C., and water or the aqueous solution is added for extraction, preferably also preheated to 50 to 90° C., in particular to 70 to 90° C. The sequence of addition can also be inverse, i.e. water or the aqueous solution can be added before the at least one aromatic solvent; or water or the aqueous solution and the at least one aromatic solvent can be added simultaneously; at least one of the two being preferably preheated to 50 to 90° C., in particular to 70 to 90° C. Heating is mainly carried out in order to improve dissolution of the components of the mixture of step (ii) in one of the two solvent systems (aromatic solvent or aqueous medium).

After extraction, i.e. after bringing the organic phase and the aqueous phase into close contact with each other, the aqueous phase and the organic phase are separated.

In step (iv), if necessary, a part of the aromatic solvent(s) introduced in step (iii) is removed from the organic phase obtained in step (iii) to such an extent that the resulting mixture contains the compound (I) in a concentration of from 30 to 90% by weight, relative to the total weight of the resulting mixture (i.e. the mixture obtained after the removal of the aromatic solvent(s)).

Step (iv) is necessary if the amount of aromatic solvent(s) introduced in step (iii) is so high that compound (I) is contained in the mixture obtained after step (iii) (to be more precise in the organic phase separated from the aqueous phase) in a concentration below 30% by weight, relative to the total weight of the mixture.

Preferably, the at least one aromatic compound is removed to such an extent that the resulting mixture contains the compound (I) in a concentration of from 40 to 65% by weight, relative to the total weight of the mixture.

The concentration of the compound (I) in the mixture is determined by standard procedures, e.g. by gas chromatography or HPLC.

The at least one aromatic compound removed in step (iv) can be recycled and used again in step (iii), if necessary after a purification step, e.g. via rectification.

Analogously, the mixture of step (a) preferably contains the compound (I) in a concentration of from 40 to 65% by weight, relative to the total weight of the mixture.

In step (b) and (v) the at least one polar aprotic solvent is added to the mixture obtained in step (a), (iii) or (iv) in such an amount that it is contained in 1 to 25% by weight, preferably in 2 to 15% by weight, more preferably in 2 to 12% by weight, in particular in 2 to 9% by weight, specifically in 2 to 8% by weight and very specifically in 3 to 8% by weight, relative to the weight of the mixture obtained after its addition.

Despite of step (ii) and the aqueous extraction in step (iii) in which the polar aprotic solvent(s) should be removed more or less completely, the mixture obtained after step (iii) or after step (iv), if the latter is necessary, may still contain traces of the polar aprotic solvent(s). Also the mixture of step (a) may contain traces of such polar aprotic solvent(s). This solvent and the amount in which this is still present can be detected by standard methods, for example via gas chromatography, and is taken into account when calculating the amount of polar aprotic solvent(s) to be added in step (b) or (v).

In a preferred embodiment, if the mixture obtained in step (a), (iii) or (iv), if the latter is necessary, contains solids visible with the naked eye, this mixture is heated before the least one polar aprotic solvent is added to obtain a mixture in which no solids are visible. Preferably, the mixture is heated to 50 to 100° C., in particular to 70 to 90° C. before the least one polar aprotic solvent is added.

Crystallization in step (c) or (vi) is carried out by known methods, e.g. by simply allowing the mixture to stand or by cooling the mixture, especially if it was heated in step (b) or (v) or, if step (b) or (v) was performed without heating, by heating and cooling again, or by reheating the cooled mixture and cooling it again. Cooling and heating can be repeated several times. Seed crystals of the compound of formula (I) can be added to the cooled solution in order to set off crystallization.

In particular, crystallization in step (c) or (vi) is performed by cooling the preheated mixture of step (b) or (v) and optionally adding seed crystals; or, alternatively, by cooling the preheated mixture of step (b) or (v), reheating and cooling again.

Cooling means generally cooling to room temperature or below, preferably to +10° C. to −10° C., in particular to +5° C. to −5° C. and specifically to 0° C. Cooling is generally carried out within 1 to 12 h, preferably within 2 to 10 h, in particular within 6 to 10 h. Cooling can be carried out continually or stepwise, i.e. in several temperature steps.

The formed crystals are recovered from the mother liquor by standard methods, e.g. by filtration, sedimentation, decantation or centrifugation. If desired, the crystals are freed from remainders of the solvent, e.g. by washing with water and/or evaporation, especially under vacuum.

The methods of the invention yield the desired 2-[4-(4-chlorophenoxy)-2-(trifluoromethyl)phenyl]-1-(1,2,4-triazol-1-yl)propan-2-ol in a purity of at least 98%, in particular at least 98.5%, more particularly at least 99%, relative to the weight of the solid product isolated after step (c) or (vi). The methods of the invention yield 2-[4-(4-chlorophenoxy)-2-(trifluoromethyl)phenyl]-1-(1,2,4-triazol-1-yl)propan-2-ol and 2-[4-(4-chlorophenoxy)-2-(trifluoromethyl)phenyl]-1-(1,2,4-triazol-4-yl)propan-2-ol in a molar ratio of at least 80:1, preferably at least 100:1, in particular at least 140:1, more particularly at least 240:1 and specifically at least 300:1.

EXAMPLES

1) Preparation of 2-[4-(4-chlorophenoxy)-2-(trifluoromethyl)phenyl]-1-(1,2,4-triazol-1-yl)propan-2-ol 555.5 g (1.69 mol) of 2-[4-(4-chlorophenoxy)-2-(trifluoromethyl)phenyl]-2-methyl-oxirane, 152.0 g (2.2 mol) of 1H-[1,2,4]-triazole, 34.0 g (0.85 mol) of NaOH (flakes) and 1381 g of DMF were charged to a 2.5 l laboratory vessel at room temperature. The mixture was heated to 115° C. over 12 h for full conversion of the oxirane starting material (yield: 92% in solution for desired isomer).

Afterwards almost the complete DMF (>95%) was removed by vacuum distillation from the reaction mixture. Salts and the remaining DMF were separated from the product by extraction with 1690 g toluene and 1039 g water at 80° C. Finally 1318 g (78%) of the toluene was removed from the product by concentrating the organic phase under vacuum.

DMF for crystallization was added to the product solution in toluene at 85° C. The DMF amount is compiled in the table below. The percentages relate to the amount of DMF contained in the obtained mixture, relative to the total weight of the mixture obtained after the respective amount of DMF has been added. Afterwards the solution in toluene/DMF was cooled to approx. 70° C., seeded with the title product and stirred over 0.5 h. The suspension was slowly cooled down to 0° C. over 8 h for crystallization of the product. The product was separated by centrifugation from the mother liquor and dried in a vacuum oven at 80° C./50 mbar.

| No. | Amount DMF [%][1] | Content of compound (I) [%][2] | Content of symmetric isomer [%][3, 4] | Yield [% of theory][5] |
|---|---|---|---|---|
| 1 | 11.2 | 99.3 | 0.4 | 70.3 |
| 2 | 8.7 | 99.1 | 0.4 | 73.0 |
| 3 | 7.0 | 99.3 | 0.7 | 79.3 |
| 4 | 4.0 | 99.0 | 0.4 | 79.5 |
| 5 | 3.5 | 99.4 | 0.3 | 83.9 |
| 6* | 0 | 92.3 | 6.5 | 80.2 |

[1]% by weight, relative to the total weight of the mixture obtained after DMF has been added
[2]% by weight, relative to the total weight of the solid product obtained after drying
[3]symmetric isomer = 2-[4-(4-chlorophenoxy)-2-(trifluoromethyl)phenyl]-1-(1,2,4-triazol-4-yl)propan-2-ol
[4]% by weight, relative to the total weight of the solid product obtained after drying
[5]% by mol, relative to the amount [mol] of oxirane (II) used
*comparative example 2) Crystallization in the Radleys Carousel Amounts used: In each case, 118 g of the organic phase comprising the product (content: 25.0%), in o-xylene Apparatus: Radleys Carousel with 250 ml flask and corresponding Teflon paddle agitator.

Procedure: Precipitated solids were dissolved at 10000 and the respective amount of polar aprotic solvent was added. The heating was turned off and the mixture was cooled down while agitating at 730 rounds/minute. After stirring overnight, precipitated solids were separated by suction filtration at room temperature (21° C.).

The solids were washed with 23.2 g o-xylene (285 g/mole educt) and dried at 25 mbar and 60° C. in a vacuum drying cabinet over night.

Results:

2a) Polar Aprotic Solvent: DMF

| No. | Amount DMF [%][1] | Content of compound (I) [%][2] | Content of symmetric isomer [%][3, 4] | Yield [% of theory][5] |
|---|---|---|---|---|
| 1* | 0 | 96.1 | 2.82 | 85.3 |
| 2 | 1.5 | 97.2 | 1.84 | 81.2 |
| 3 | 2.9 | 96.0 | 2.40 | 76.3 |
| 4 | 4.3 | 97.1 | 1.19 | 69.7 |
| 5 | 5.7 | 96.7 | 1.65 | 67.0 |
| 6 | 7.0 | 97.8 | 1.16 | 59.0 |

2b) Polar Aprotic Solvent: NMP

| No. | Amount NMP [%][1] | Content of compound (I) [%][2] | Content of symmetric isomer [%][3, 4] | Yield [% of theory][5] |
|---|---|---|---|---|
| 1* | 0 | 96.6 | 2.46 | 85.7 |
| 2 | 1.5 | 96.6 | 1.32 | 79.8 |
| 3 | 2.9 | 96.5 | 2.14 | 74.9 |
| 4 | 4.3 | 98.2 | 0.84 | 68.6 |
| 5 | 5.7 | 98.1 | 0.84 | 64.6 |
| 6 | 7.0 | 97.9 | 0.91 | 57.8 |

Explanations for *, [1], [2], [3], [4], [5] see above.

We claim:

1. A method for obtaining 2-[4-(4-chlorophenoxy)-2-(trifluoromethyl)phenyl]-1-(1,2,4-triazol-1-yl)propan-2-ol of formula (I) from a mixture containing the compound of formula (I) and 2-[4-(4-chlorophenoxy)-2-(trifluoromethyl)phenyl]-1-(1,2,4-triazol-4-yl)propan-2-ol of formula (I-sym)

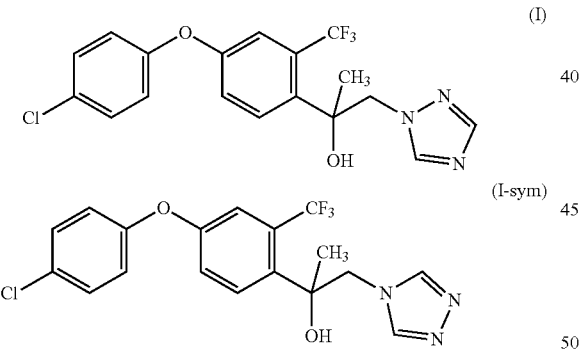

which method comprises
(a) providing a mixture containing the compounds of formulae (I) and (I-sym) in at least one aromatic solvent, where the mixture contains the compound of formula (I) in a concentration of from 30 to 90% by weight, relative to the total weight of the mixture;
(b) adding to the mixture of step (a) at least one polar aprotic solvent, so that it is contained in an amount of from 1 to 25% by weight, relative to the weight of the solution obtained after the addition of the at least one polar aprotic solvent selected from N,N-dimethylformamide, N,N-dimethylacetamide, dimethylsulfoxide and N-methylpyrrolidone; and
(c) crystallizing the compound of formula (I) from the mixture obtained in step (b).

2. A method for the preparation of 2-[4-(4-chlorophenoxy)-2-(trifluoromethyl)phenyl]-1-(1,2,4-triazol-1-yl)propan-2-ol of formula (I)

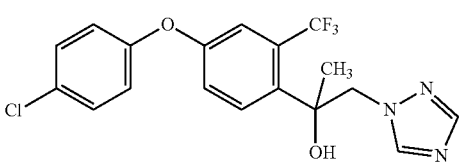

comprising:
(i) reacting 2-[4-(4-chlorophenoxy)-2-(trifluoromethyl)phenyl]-2-methyl-oxirane of formula (II)

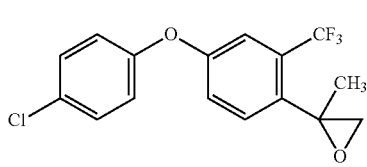

with 1H-[1,2,4]-triazole in the presence of a base in at least one polar aprotic solvent selected from N,N-dimethylformamide, N,N-dimethylacetamide, dimethylsulfoxide and N-methylpyrrolidone;
(ii) after completion of the reaction, removing at least 90% of the at least one polar aprotic solvent;
(iii) diluting the mixture obtained in step (ii) with at least one aromatic solvent and extracting the diluted mixture with water or an aqueous solution;
(iv) if necessary, removing a part of the aromatic solvent introduced in step (iii) from the organic phase obtained in step (iii) to such an extent that the resulting mixture contains the compound (I) in a concentration of from 30 to 90% by weight, relative to the total weight of the mixture;
(v) adding to the mixture obtained in step (iii) or (iv) at least one polar aprotic solvent selected from N,N- dimethylformamide, N,N-dimethylacetamide, dimethylsulfoxide and N-methylpyrrolidone, so that it is contained in an amount of from 1 to 25% by weight, relative to the weight of the mixture obtained after the addition of the at least one polar aprotic solvent; and (vi) crystallizing the compound of formula (I) from the mixture obtained in step (v).

3. The method as claimed in claim 2, where the base used in step (i) is an inorganic base selected from LiOH, NaOH, KOH, $Li_2CO_3$, $Na_2CO_3$, $K_2CO_3$, $Cs_2CO_3$, $Li_3PO_4$, $Na_3PO_4$ and $K_3PO_4$.

4. The method as claimed in claim 3, where the base is LiOH, NaOH or KOH and is used in an amount of from 0.2 to 1 mol per mol of compound (II).

5. The method as claimed in claim 2, where step (i) is carried out at from 110 to 130° C.

6. The method as claimed in claim 2, where the at least one polar aprotic solvent used in step (i) and (v) is N,N-dimethylformamide.

7. The method as claimed in claim 2, where in step (ii) at least 92% of the at least one polar aprotic solvent are removed.

8. The method as claimed in claim 2, where in step (ii) the at least one polar aprotic solvent is removed to such an extent that in the resulting mixture the weight ratio of the remaining at least one polar aprotic solvent to theoretically present compound (I) is from 1:3 to 0:1.

9. The method as claimed in claim 2, where the at least one aromatic solvent used in step (iii) is selected from benzene, toluene, the xylenes and mixtures thereof.

10. The method as claimed in claim 2, where in step (iii) the diluted mixture is extracted with water or brine.

11. The method as claimed in claim 2, where the extraction in step (iii) is carried out at from 50 to 90° C.

12. The method as claimed in claim 2, where in step (iv) the at least one aromatic compound is removed to such an extent that the resulting mixture contains the compound (I) in a concentration of from 40 to 65% by weight, relative to the total weight of the mixture.

13. The method as claimed in claim 2, where in step (v) the at least one polar aprotic solvent selected from N,N-dimethylformamide, N,N-dimethylacetamide, dimethylsulfoxide and N-methylpyrrolidone is added in an amount of from 2 to 12% by weight relative to the weight of the mixture obtained after the addition of the at least one polar aprotic solvent.

14. The method as claimed in claim 2, where in step (v) the mixture obtained in step (a), (iii) or (iv) is heated before the least one polar aprotic solvent selected from N,N-dimethylformamide, N,N-dimethylacetamide, dimethylsulfoxide and N-methylpyrrolidone is added to obtain a mixture in which no solids are visible.

15. The method as claimed in claim 14, where in step (b) and (v) the mixture obtained in step (iii) or (iv) is heated to 50 to 100° C. before the least one polar aprotic solvent selected from N, N-dimethylformamide, N,N-dimethylacetamide, dimethylsulfoxide and N-methylpyrrolidone is added.

16. The method as claimed in claim 2, where crystallization in step (vi) is performed by cooling the preheated mixture of step (v) and optionally adding seed crystals; or by cooling the preheated mixture of step (v), reheating and cooling again.

17. The method as claimed in claim 1, where the at least one polar aprotic solvent used in step (b) is N,N-dimethylformamide.

18. The method as claimed in claim 1, where the at least one aromatic solvent used in step (a) is selected from benzene, toluene, the xylenes and mixtures thereof.

19. The method as claimed in claim 1, where in step (b) the at least one polar aprotic solvent selected from N,N-dimethylformamide, N,N-dimethylacetamide, dimethylsulfoxide and N-methylpyrrolidone is added in an amount of from 2 to 12% by weight relative to the weight of the mixture obtained after the addition of the at least one polar aprotic solvent.

20. The method as claimed in claim 1, where in step (b) the mixture obtained in step (a) is heated before the least one polar aprotic solvent selected from N,N-dimethylformamide, N,N-dimethylacetamide, dimethylsulfoxide and N-methylpyrrolidone is added to obtain a mixture in which no solids are visible.

21. The method as claimed in claim 20, where in step (b) the mixture obtained in step (a) is heated to 50 to 100° C. before the least one polar aprotic solvent selected from N,N-dimethylformamide, N,N-dimethylacetamide, dimethylsulfoxide and N-methylpyrrolidone is added.

22. The method as claimed in claim 1, where crystallization in step (c) is performed by cooling the preheated mixture of step (b) and optionally adding seed crystals; or by cooling the preheated mixture of step (b), reheating and cooling again.

\* \* \* \* \*